United States Patent
Fortin et al.

(10) Patent No.: US 8,114,025 B2
(45) Date of Patent: Feb. 14, 2012

(54) DEVICE AND METHOD FOR CONTROLLING THE PRESSURE IN AN INFLATABLE CUFF OF A BLOOD PRESSURE MANOMETER

(75) Inventors: Juergen Fortin, Graz (AT); Rupert Gruellenberger, Graz (AT); Alexander Hacker, Unterpremstaetten (AT); Falko Skrabal, Graz (AT)

(73) Assignee: CNSystems Medizintechnik GmbH, Graz (AT)

( * ) Notice: Subject to any disclaimer, the term of this patent is extended or adjusted under 35 U.S.C. 154(b) by 1415 days.

(21) Appl. No.: 10/576,513

(22) PCT Filed: Aug. 19, 2004

(86) PCT No.: PCT/AT2004/000289
§ 371 (c)(1),
(2), (4) Date: Apr. 20, 2006

(87) PCT Pub. No.: WO2005/037097
PCT Pub. Date: Apr. 28, 2005

(65) Prior Publication Data
US 2007/0032729 A1      Feb. 8, 2007

(30) Foreign Application Priority Data
Oct. 21, 2003 (AT) .................................. 1671/2003

(51) Int. Cl.
*A61B 5/02* (2006.01)
(52) U.S. Cl. ........................................ 600/485; 600/490
(58) Field of Classification Search .................. 600/485, 600/490–499
See application file for complete search history.

(56) References Cited

U.S. PATENT DOCUMENTS
3,905,354 A * 9/1975 Lichowsky .................. 600/494
(Continued)

FOREIGN PATENT DOCUMENTS
EP            0 537383         4/1993
(Continued)

OTHER PUBLICATIONS

Abstract of Article Entitled "Non-Invasive Continuous Blood Pressure Monitoring by the Unloading of Vascular Wall" by Wang et al. In IEEE Engineering in Medicine & Biology Society, 11th Annual Conference, Nov. 9, 1989.

*Primary Examiner* — Patricia Mallari
*Assistant Examiner* — Christian Jang
(74) *Attorney, Agent, or Firm* — Dykema Gossett PLLC

(57) ABSTRACT

The invention relates to a method and a device for regulating the pressure in at least one inflatable cuff, preferably a finger cuff (6), of a blood pressure manometer comprising a plethysmographic sensor device (8, 9) for detecting a plethysmographic signal PG and a pressure sensor (7) for detecting a cuff pressure signal BP. According to the invention, two control loops (1, 2) acting on a differential amplifier (10) are used to independently regulate different operating parameters, the first, inner control loop (1) using the cuff pressure signal BP as the first regulating variable, and the second, outer control loop (2) comprising a regulating device (12), preferably a PID regulator, which generates a nominal value SW as a second regulating variable from the plethysmographic signal PG. The differential amplifier (10) is connected, on the output side, to at least one valve connected to a pressure source (4), preferably a proportional valve (3; 25, 27), for regulating the pressure in the cuff (6). Additional outer control loops (16 to 21) can be used to respectively set a parameter of the device to a determined nominal value.

18 Claims, 2 Drawing Sheets

U.S. PATENT DOCUMENTS

| | | |
|---|---|---|
| 4,406,289 A | 9/1983 | Wesseling et al. |
| 4,459,991 A * | 7/1984 | Hatschek ................ 600/494 |
| 4,510,940 A * | 4/1985 | Wesseling ................ 600/480 |
| 4,539,997 A | 9/1985 | Wesseling et al. |
| 6,500,127 B1 | 12/2002 | Inukai et al. |
| 7,367,949 B2 * | 5/2008 | Korhonen et al. ............ 600/483 |
| 2002/0169381 A1 * | 11/2002 | Asada et al. ................ 600/485 |

FOREIGN PATENT DOCUMENTS

WO      0059369      10/2000

* cited by examiner

DEVICE AND METHOD FOR CONTROLLING THE PRESSURE IN AN INFLATABLE CUFF OF A BLOOD PRESSURE MANOMETER

BACKGROUND OF THE INVENTION

1. Field of the Invention

The invention relates to a device and a method for controlling the pressure in at least one inflatable cuff, preferably a finger cuff, of a blood pressure measuring apparatus provided with a plethysmographic sensing device, where a plethysmographic signal PG and a cuff pressure signal BP are obtained.

2. The Prior Art

The continuous monitoring of blood pressure in an artery in a non-invasive way has for years been of interest to scientists and researchers. As early as in 1942 R. Wagner in Munich presented a mechanical system which was designed to measure arterial pressure of the arteria radialis by means of the so-called "vascular unloading technique", which is also known as the principle of the relaxed arterial wall (Wagner R. "Methodik und Ergebnisse fortlaufender Blutdruckschreibung am Menschen", Leipzig, Georg Thieme Verlag, 1942; Wagner R. et al. "Vereinfachtes Verfahren zur fortlaufenden Aufschrift des Blutdruckes beim Menschen", Zschr. Biol. 112, 1960). The method for non-invasive blood pressure determination presented by J. Penaz in Dresden in 1973 (Digest of the $10^{th}$ Inter-national Conference on Medical and Biological Engineering 1973 Dresden), also employs the vascular unloading technique. Due to this technique it was possible for the first time to continuously record—albeit only for a short period—the intra-arterial blood pressure with the use of an electro-pneumatic control loop. In this method light is shone through a finger and pressure is applied to the finger via a servo-control system in such a way that the originally pulsating flow registered by the transmitted light is kept constant.

The method in principle is based on the following control loop: a limb or part of the human body containing an artery, such as a finger, carpus or the temple, is shone through by light from a light source. The light which passes through the limb (e.g. finger) or is reflected by a bone contained in the limb or body part (e.g. carpus, temple) is detected by a suitable light detector and provides an inverse measure for the volume of blood in the extremity (plethysmographic signal PG). The more blood there is in the extremity, the more light is absorbed and the smaller is the plethysmographic signal PG. The mean value of PG is suppressed by a difference amplifier, and the resulting signal PG is fed to a controller unit. In the method of Penaz this controller has a proportional-integral-differential (PID) characteristic. The control signal generated by the PID-controller is amplified and added to a constant set-point value (SP) and fed to a servo-or proportional-valve, which generates pressure in a cuff, which in turn acts on the extremity shone through by the light. The control system is such that the plethysmographic signal PG is kept constant over time by means of the pressure applied. When the heart pumps more blood into the extremity during systole and the PG signal exhibits a tendency to decrease, the PID-controller increases its control signal, and pressure in the cuff rises until the surplus blood is pushed out of the extremity and the PG signal reverts to its previous value. Conversely, when the blood flow into the extremity decreases during diastole with the heart in its fill-up phase, which would lead to a rise in the PG signal, the control signal of the PID controller decreases and causes the pressure applied to the finger to drop. Thus the plethysmographic signal is kept constant. By this control system, which keeps the PG signal and thereby the volume of blood in the extremity constant over time, the pressure difference (transmural pressure) between the intra-arterial pressure and the applied external pressure is zero. Thus the externally applied pressure, i.e. the cuff pressure BP, equals the intra-arterial pressure in the extremity. This permits indirect measurement of the blood pressure by means of a pressure sensor or manometer.

The above description of the Penaz principle assumes the control system to be in "closed loop" operation. The system may also operate under "open loop" conditions, with the control signal of the PID controller not added to the set-point value SP. The pressure in the cuff now does not depend on the plethysmographic signal PG and is solely determined by the set-point value SP. According to Penaz, SP corresponds to the mean arterial pressure in the extremity and is characterised by maximal pulsation of the PG value.

This photo-plethysmographic method has been used in a number of further procedures and devices for the measurement of blood pressure. EP 0 537 383 A1 shows an inflatable finger cuff for non-invasive continuous monitoring of blood pressure. The inflatable cylindrical space of the cuff is pneumatically connected to a fluid source. An infrared light source and a detector are positioned on opposite sides of the finger in a rigid cylinder. There is furthermore provided a valve for filling the cylinder with a gas. Electrical leads for the light source and the detector are passed through the cylinder wall. U.S. Pat. Nos. 4,510,940 A and 4,539,997 A also show devices and methods for continuous, non-invasive blood pressure measurement. A fluid-filled cuff, a light source, a light detector and a difference pressure amplifier are provided. Similar devices for blood pressure measurement are known from U.S. Pat. No. 4,406,289 A.

From WO 00/59369, whose subject is a continuous, non-invasive blood pressure measuring apparatus, an improvement of the proportional valve or rather the pressure generating system is known, together with variants of pressure cuffs for diverse extremities.

All known methods and devices—while partly proposing substantial improvements concerning cuff, proportional valve, determination of the set-point SP, etc.—have one thing in common with the original measuring principle of Penaz: a relatively simple control system operated in "closed loop" mode with a controller, e.g. a PID controller. The control system described by Penaz presents a challenge to automatic control engineering. The following independent systems each with specific disturbance variables are part of the control system:

Pressure generation with pressure source (pump) and proportional valve—pump pressure and valve leakage may vary.

Pressure chamber, cuff and pressure transmission to the arterial blood vessel via the tissue of the extremity.

Pulsating fluctuations of blood flow due to the action of the heart—this is the intended disturbance variable, which is to be compensated by the cuff pressure in accordance with Penaz's principle.

If the extremity used is the finger, the arterial blood vessel is a so-called resistance vessel. This means that the diameter of the artery—and thus the blood volume—may be increased (vasodilatation) or decreased (vasoconstriction) by the autonomous nervous system via the smooth muscles of the vessel wall.

Light source and light detection system. Disturbance variables here are manufacturing tolerances of the parts used and above all the influence of ambient light on the plethysmographic signal PG.

Mean value suppression of the PG signal.

Further disturbances due to fluctuations in the parts used, or due to electrical or mechanical influences.

These factors almost preclude the possibility of continuous blood pressure measurement according to the Penaz principle over a long period of time, even if the set-point SP is optimally determined under open loop operation.

In U.S. Pat. No. 4,510,940 A an effort was made to cope with these disadvantages. A method for long-time blood pressure measurement is described, in which closed loop operation is interrupted periodically and SP is newly determined under open loop operation. This method is a compromise and has the disadvantage that blood pressure fluctuations occurring during the periodic search for optimum SP are not detected.

It is the aim of the present invention to propose, based on the initially described methods and devices, an improved control procedure and a corresponding apparatus for blood pressure measurement implementing the procedure, in which a plethysmographic signal PG and a cuff pressure signal BP are obtained. In particular, long-time indirect measurement of continuous blood pressure is to be guaranteed.

The invention achieves this aim by
a) using the cuff pressure signal BP in a first, inner control loop as control variable and feeding it as a first input signal into a difference amplifier,
b) feeding the plethysmographic signal PG, with mean value $\overline{PG}$ suppressed, into a controller, preferably a PID controller, in a second, outer control loop, adding a set-point signal SP and generating a target signal SW, which is fed as a second input signal into the difference amplifier, and
c) by using the output signal AS of the difference amplifier to control at least one valve connected to a pressure source, i.e. preferably a proportional valve, which in turn regulates the pressure in the cuff.

A device for controlling the pressure in at least one inflatable cuff, preferably a finger cuff, of a blood pressure measuring apparatus, which has a plethysmographic sensor device for obtaining a plethysmographic signal PG and a pressure sensor for obtaining a cuff pressure signal BP, is characterised in that two control loops acting on a difference amplifier are provided, where the first, inner control loop uses the cuff pressure signal BP as a first control variable and where the second, outer control loop is provided with a controller, preferably a PID-controller, which generates a target variable SW from the plethysmographic signal PG as a second control variable, and where the output of the difference amplifier controls at least one valve which is connected to a pressure source, i.e. preferably a proportional valve, thereby regulating the pressure in the cuff. The second control loop is provided with a difference amplifier of known design, which subtracts the plethysmographic signal PG from its mean value $\overline{PG}$, and with a summation unit (13) adding a set-point signal SP.

The present invention describes a novel control procedure which will permit long-time indirect measurement of continuous blood pressure. The control procedure can be realised either as electronic circuitry or it may be implemented on a computer having program and data-storage capabilities. Peripheral control loops can preferentially be implemented on a computer in program form, while faster, inner control loops containing the drivers for the pressure generation system or for the light-generation and light-detection systems, are preferably realised as electronic circuits. A precise distinction between software and electronic circuitry will not be required in the context of the invention.

The basic principle of the proposed control procedure consists in providing specific control loops, which are preferably concentric, for precisely defined temporal properties and parameters of the whole control system (fast pressure build-up and decrease, compensation of transmural pressure over a single heart cycle, medium-term fluctuations, long-term drifts). Concentric in this case means that the inner control loop is pertinent to a certain temporal property or parameter of the control system and presents idealised conditions for this temporal property to the immediately following outer control loop. This immediately following outer loop may act as an inner loop for yet another outer loop. Preferentially, the inner loops take care of fast control tasks, while the outer loops are responsible for the long-term stability of the overall control system. Furthermore, there may be provided dedicated control loops for certain specific quantities (e.g. cuff pressure, light detection system, mean value suppression etc.), with control parameters optimised for the respective disturbing variable. These control loops need not necessarily be concentric in the sense explained above.

The invention will now be explained in more detail with reference to the enclosed drawings.

DETAILED DESCRIPTION OF THE PREFERRED EMBODIMENTS

Figure 1:
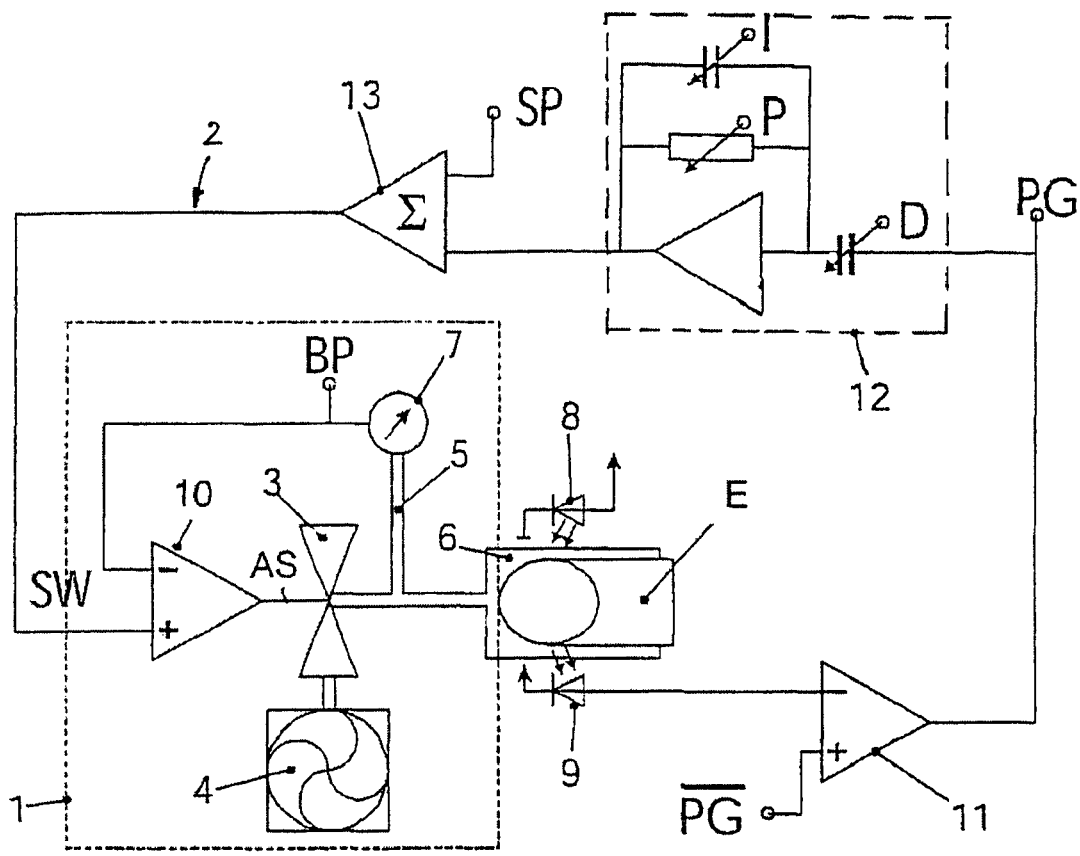
FIG. 1 schematically shows a device according to the invention for controlling the pressure in an inflatable cuff of a blood pressure measuring apparatus with two control loops.

FIG. 1 shows a device for controlling pressure in an inflatable finger cuff 6 of a blood pressure measuring apparatus not further shown here. The control system consists of a first, inner control loop 1, which receives a target signal SW from a second, outer control loop 2. The inner control loop 1 comprises a difference amplifier 10 (preferably an operational amplifier), a proportional valve 3, which receives pressure from a pressure source, e.g. a pump 4, a pressure chamber 5 connected to the cuff 6, and a pressure sensor 7, which converts the pressure generated in the pressure chamber 5 or in the cuff 6 into an electrical signal BP, proportional to the cuff pressure. This electrical signal BP, which represents the intra-arterial pressure curve in the extremity E, is fed into the difference amplifier 10, whereby the first, inner control loop is closed. The difference amplifier 10 adjusts its output voltage AS in such a way that the voltage between its + input and its − input tends to zero. The difference amplifier 10 adjusts the pressure in the cuff 6 via the proportional valve 3 in such a way that the voltage produced by the pressure sensor 7 equals the target value SW.

The second, outer control loop 2 supplies a target value SW corresponding to the actual pressure at the extremity E (e.g. the finger), which is necessary to keep the plethysmographic signal PG of the plethysmographic sensor device 8,9 constant. The outer control loop 2 is now no longer responsible for the specific properties of the pressure generation system consisting of proportional valve 3, pump 4, pressure chamber 5, cuff 6 and the pressure sensor or manometer 7, and comprises essentially the plethysmographic sensor device, i.e. the light source 8 (preferably LEDs) and the light detector 9 (preferably a photodiode), which determine the volume of blood in the extremity E in a known way, and a difference amplifier 11, which subtracts the signal PG from its mean value $\overline{PG}$, and a controller 12, whose control parameters, proportional amplification P, integral amplification I and/or differential amplification D can be adjusted. The outer control loop 2 is closed via a summation unit 13, which adds the controlled signal to the preset set-point signal SP and thus supplies the target value SW for the inner control loop 1.

The simple presentation of the control procedure of the invention given in FIG. 1 shows the following advantage as compared with the initially described methods: the inner control loop 1 is optimised for fast pressure changes, while the outer control loop 2 is exclusively dedicated to the compensation of the plethysmographic signal PG. The parameters of the individual control loops may thus be optimised for their respective tasks. A further difference, which will be elaborated on later, is the fact that here there is no sharp distinction between open and closed loop operation. In the procedure of the invention open loop operation is given if the loop amplifications P, I and D of the PID-controller 12 are set to zero. For all other settings of these parameters the control loop 2 is closed.

If long-term changes of the system are to be compensated as well, further control loops, each responsible for a specific task, may be added. Control loops which compensate certain changes over time (slow medium-to long-term drifts, but also faster changes in pressure) during blood pressure recording (closed loop operation) are preferably designed as concentric loops in the sense explained above. Control loops or procedures which serve to define certain initial conditions (initial values for SP, P, I and D, settings of the light detection system, mean value suppression of PG, etc.) for the measurement proper, do not necessarily have to be concentric.

Figure 2:
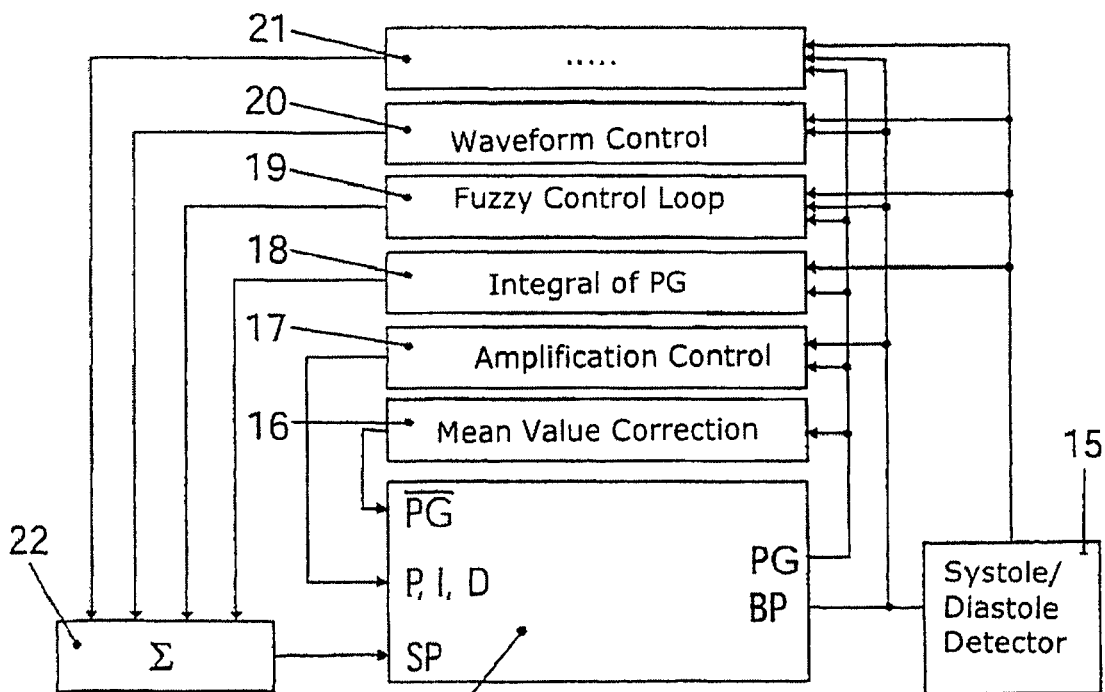
FIG. 2 shows an extended variant of a device as in FIG. 1 with additional control loops.

FIG. 2 shows a possible further development of the two control loops 1 and 2 based on the basic design shown in FIG. 1. The control loops 16 to 21 shown here need not all be present and their sequence may be changed. The schematic presentation of FIG. 2 is supposed to illustrate the basic principle of concentric control loops together with the novel features as compared with the state of the art. Preferably control loops which act more frequently on the system as a whole and therefore are responsible for faster changes, should be designed as inner loops.

The control system with loops 1 and 2 as shown in FIG. 1 is represented in FIG. 2 as the central control system 14 and has input parameters SP, $\overline{PG}$, P, I and D, and output parameters BP and PG. Around this central control system 14 further concentric controllers may be used without necessitating an interruption of measurement in order to determine new initial conditions under open loop operation, as is the case in U.S. Pat. No. 4,510,940 A. In U.S. Pat. No. 4,539,997 A cited above, a first and second control loop are also mentioned in a purely formal way, but contrary to the present invention, what is meant there is only the known closed control loop with a PID-controller and an open control loop without controller.

The invention proposes that the cuff pressure signal BP is fed to a systole/diastole detector, whose output signal is used as control variable in at least one of the control loops 3 to 8 to be described below. The point in time of the systoles or diastoles of blood pressure, which is required for certain control loops, is supplied by this detector.

The invention also provides for instance that in a third control loop (mean value correction 16) the mean value $\overline{PG}$ of the plethysmographic signal PG is determined and continuously corrected as input signal of the second control loop. This controller determines the mean value of PG and, if necessary, adjusts it at the $\overline{PG}$ input of the second control loop.

In a further development of the invention the amplification parameters P, I and/or D are optimised in a fourth control loop (amplification control 17), using the plethysmographic signal PG and the cuff pressure signal BP, and are continuously corrected as inputs to the PID-controller 12. This control loop is dedicated to monitoring and, if necessary, correcting the loop amplifications P, I and D of the second control loop. To this end the ratio between cuff pressure signal BP and plethysmographic signal PG is continuously monitored and optimised.

In an advantageous variant of the invention the set-point signal SP is readjusted in a fifth control loop 18 depending on the integral of the plethysmographic signal PG. Here the integral of PG is computed for the time period between two diastoles. Despite continuous compensation a small PG-signal is always present as an actuating signal and its integral can be computed. Since the control system of the whole system requires that the plethysmographic signal PG be kept constant by the pressure applied, the integral of PG over time, i.e. over one heart cycle, must also be constant. If this is not the case control loop 18 will act on the system and will change the applied pressure by changing the set-point SP.

In a further development of the invention the set-point signal SP is readjusted in a sixth control loop (fuzzy control loop 19) on the basis of derived quantities such as amplitude, mean value, signal waveform, etc. of the plethysmographic signal PG and of the cuff pressure signal BP, using a fuzzy-logic approach. The fuzzy controller 19 compares new heart cycles, demarcated by the systole/diastole detector 15, with preceding heart cycles. Here both signals BP and PG are monitored. In accordance with fuzzy logic the following fuzzy heuristics may for instance be formulated:

BP resp. PG has (strongly) increased/decreased, therefore SP is adjusted upwards/downwards, the ratio of mean pressure to pressure amplitude has become greater/smaller, therefore SP is adjusted upwards/downwards, the ratio of mean pressure to diastolic pressure has become greater/smaller, therefore SP is adjusted upwards/downwards.

and so on.

According to the invention the set-point signal SP is readjusted in a seventh control loop 20 depending on the waveform of the pulse of the cuff pressure signal BP. The controller 20 "waveform control" also compares the new heart cycles demarcated by the systole/diastole detector 15 with preceding ones, the shape of the cuff pressure signal BP being monitored and compared with the pulse waveform of preceding heart cycles. As is well known, the pulse waveform differs from patient to patient, each patient having a characteristic waveform, just as he has a characteristic finger print. The pulse waveform depends on the condition of large and small blood vessels and may change in the course of the years, but not during the time of a blood pressure measurement. This property may also be used in controlling the cuff pressure. If the pulse waveform changes over time, a physiological vaso-constriction or vaso-dilatation has probably occurred and the set-point, respectively the set-point signal SP, must be readjusted.

Finally, neural networks, autoregressive models or self-teaching models may be employed to readjust the set-point signal in an eighth control loop 21.

The summation unit 22 (FIG. 2) adds the changes of the set-point SP supplied by the individual control loops 16 to 17 and readjusts the pressure applied to the extremity E via the SP-input of the second control loop 2 (FIG. 1).

Figure 3:
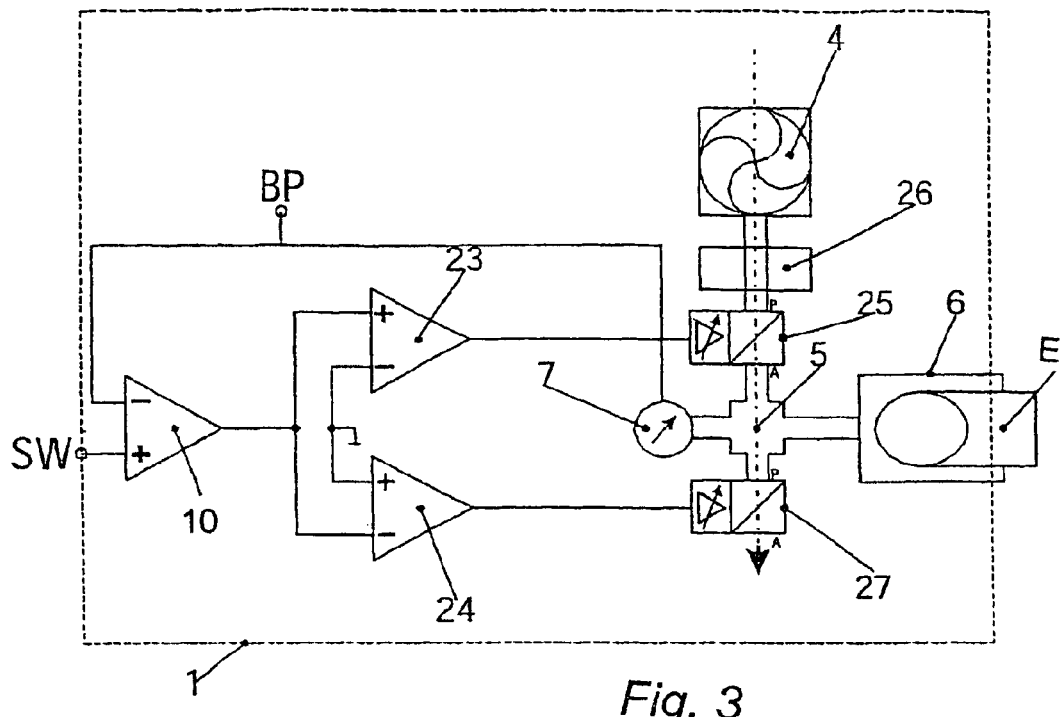
FIG. 3 shows a variant of the invention with separate intake and outlet valves of the inflatable cuff.

FIG. 3 shows an embodiment of the invention in which the difference amplifier 10 controls an inlet valve 25 connected to a pressure source 4 via an non-inverting amplifier unit 23 and an outlet valve 27 via an inverting amplifier unit 24, the valves preferably being proportional valves which are pressure-connected to the inflatable cuff 6. Instead of one proportional valve 3 (as in FIG. 1) two separate valves—one for pressure increase, one for pressure decrease—are used in this case. The advantage of this configuration, though without the use of multiple control loops, is described in WO 00/59369 A2 cited above.

The alternative control loop 1 shown in FIG. 3, which is supplied with a target value SW, consists of a difference amplifier 10 (preferably an operational amplifier) acting as controller. The output voltage of the difference amplifier 10 drives a non-inverting amplifier unit 23 and an inverting amplifier unit 24. Absolute amplification of both units is equal, and thus the output voltage of one unit is equal to the negative voltage of the other, $$U_1 = -U_2.$$

The amplifier unit 23 controls a proportional inlet valve 25, which on one side is connected to the pump 4 via a pressure compensation vessel 26. This inlet valve 25 controls the entry pressure into a pressure chamber 5, which is pressure-connected to the cuff 6. The amplifier unit 24 controls a proportional outlet valve 27, which on one side is connected to the pressure chamber 5. This outlet valve 27 controls the outlet pressure of the pressure chamber 5 against normal atmospheric pressure. If the output voltage of the difference amplifier 10 increases, the output voltage of the non-inverting amplifier unit 23 will increase and the output voltage of the inverting amplifier unit 24 will decrease by the same amount. Thus the inlet valve 25 will be opened and the outlet valve 27 will be closed to the same degree. Pressure in the cuff 6 will rise rapidly. If the output voltage of the difference amplifier 10 decreases the opposite will happen. The outlet valve 27 will be opened via the inverting amplifier unit 24 and the inlet valve 25 will be closed via the non-inverting amplifier unit 23 by the same amount, causing a pressure decrease in the pressure chamber 5 and in the cuff 6. A pressure sensor or manometer 7 converts the pressure generated in the presssure chamber 5 into the cuff pressure signal BP, which is proportional to the pressure and is fed into the difference amplifier 10, whereby the first control loop is closed. Ideally the difference amplifier 10 adjusts its output voltage in such a way that the voltage between its +input and its −input tends to zero. The difference amplifier 10 steers the inlet valve 25 and the outlet valve 27 via the amplifier units 23 and 24 in such a way that the voltage generated by the pressure sensor 7 equals the target value SW.

The circuit shown in FIG. 3 advantageously works also with non-linear valves 25 and 27 and even with fast digital on/off switching valves. According to the invention the difference amplifier 10 may be designed as a comparator, which actuates at least one digital switching valve regulating the pressure in the cuff 6. The comparator in this case acts as an operational amplifier with maximum amplification (without amplification feedback). The comparator 10 compares SW and BP. If BP is less than SW the output voltage is approximately equal to the positive operating voltage, and the inlet valve 25 is completely opened via the amplifier unit 23 and the outlet valve 27 is completely closed via the amplifier unit 24. The pressure generated in the pressure chamber 5 increases until BP is greater than SW. The output voltage of the difference amplifier (comparator) 10 is then approximately equal to the negative operating voltage and the inlet valve 25 is completely closed while the outlet valve 27 is completely open. The pressure generated in the pressure chamber 5 decreases. If SW and BP are approximately equal a rectangular pulse train with a pulse/space ratio of 50% will be generated at the output of the difference amplifier (comparator) 10.

Information regarding pressure decrease or increase is thus encoded in the pulse/space ratio of the rectangular pulse train generated at the output of the difference amplifier (comparator) 10. A precondition for the functioning of the system are sufficiently fast switching valves (preferably piezo-valves), which react much faster than the pressure change in the cuff 6, which is characterised by a certain inertia.

The control loops shown in FIGS. 1 to 3 all are active during continuous blood pressure measurement (closed loop operation). To guarantee correct operation precisely defined initial conditions must be established—as is the case for most control loops. The initial conditions are preferably determined prior to the measurement proper. It is of no import wether this is done in open loop or closed loop operation.

In contrast to the state-of-the-art methods mentioned before, it will be of advantage in the invention if an optimum plethysmographic signal PG is found. The invention therefore provides that the plethysmographic sensor 8, 9 is furnished with a device 28, 40, 41 for the elimination of stray light, in particular ambient light, from the plethysmographic signal PG, and further provides circuitry 33 to 38 for controlling the voltage or current of the light source 8 of the plethysmographic sensor.

Figure 4:
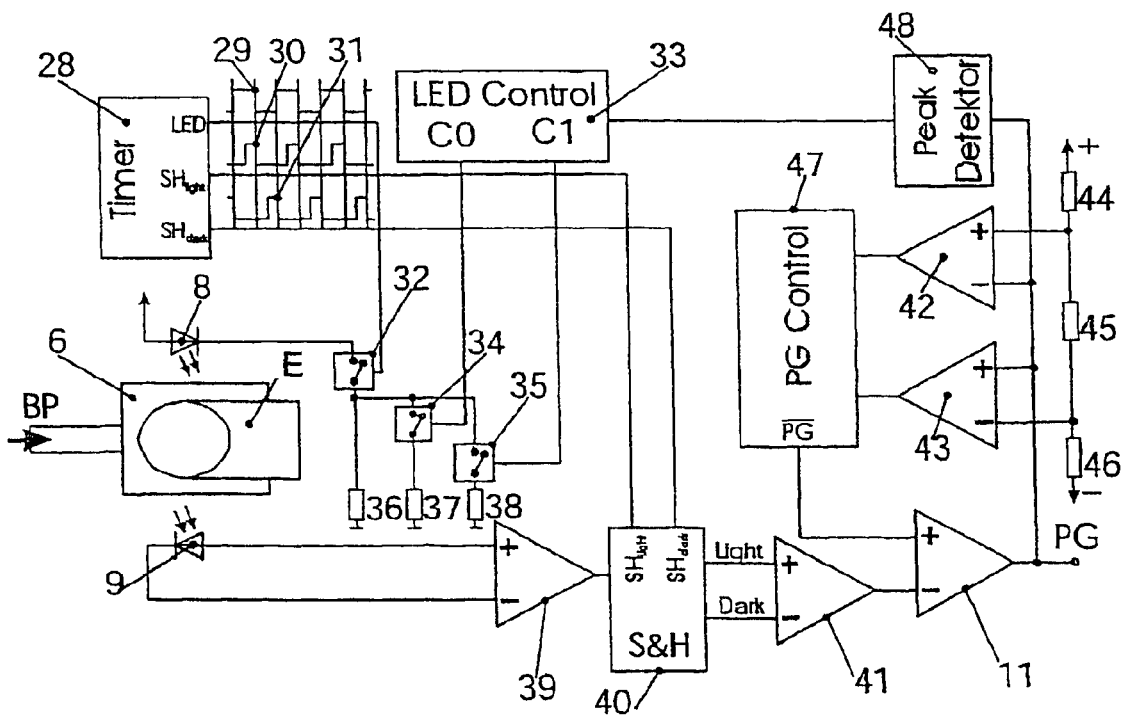
FIG. 4 shows circuitry details of a further variant of the invention.

FIG. 4 shows a possible variant of a control system generating an optimal PG-signal. That part of the system which eliminates ambient light, is a concentric control loop, the part which sets the optimal LED-current (light source 8), however, is not, since it defines an initial value.

The light source 8, a LED, is controlled by a timer unit 28, which generates three synchronous rectangular pulse trains. The signal "LED" 29 pulsatingly activates the LED 8. When the signal "LED" 29 is at HIGH the LED 8 is turned on. The pulse/space ratio of 50% shown in FIG. 4 is not essential, and other ratios are possible. The timer 28 furthermore generates a signal "$SH_{light}$" 30 (Sample & Hold), which is HIGH immediately before the LED 8 is turned off. The signal "$SH_{dark}$" 31 also generated by the timer is HIGH immediately before the LED 8 is turned on.

The signal 29 turns on the LED 8 by means of switch 32. The unit LED-control 33 can change the current of LED 8 and thus the light intensity. Switches 34 and 35 can be used to activate the shunt resistors 37 and 38 parallel to the current limiting resistor 36, and thereby the total current through LED 8 can be increased.

The light which is shone through the extremity E, is detected by a photodiode 9 and amplified by an amplifier 39. The detected light signal will pulsate as the LED 8 is turned on and off. But a weak light signal will be detected even if the LED 8 is off, because ambient light will also pass through the extremity E and generate a signal at the photodiode 9. In order to avoid transients caused by turning the LED 8 on and off, the time immediately prior to the switching of LED 8 will now be considered. Immediately before LED 8 is turned on—LED 8 is still dark—the signal generated in the photodiode 9 depends solely on ambient light. On the other hand, immediately before LED 8 is turned off—with LED 8 still emitting light—the signal generated in the photodiode 9 will depend on the light of the LED plus ambient light. These points in time are defined by the timer 28 and its signals "$SH_{light}$" 30 and "$SH_{dark}$" 31. The amplified light signal of the photodiode 9 is fed to a sample&hold unit 40 and demodulated by the signals "SH$_{light}$" 30 and "SH$_{dark}$" 31. At the output terminals of the sample&hold unit 40 the signals Light and Dark are generated. If the difference of these two signals is computed in a difference amplifier 40, there will result a light signal which is only dependent on the light intensity of the LED 8 and is free of ambient light effects.

The light signal generated has a predominating DC-component and an added smaller signal PG, which is the desired plethysmographic signal corresponding to the pulsating changes of blood volume due to the action of the heart. The DC-component or rather the mean value of the PG-signal $\overline{PG}$ is not relevant for the blood pressure measurement proper, but is a disturbance and must therefore be suppressed. $\overline{PG}$ is however dependent on the extremity E chosen for measurement and differs greatly between patients. According to the invention the control system therefore is furnished with a device 42 to 47 for computing a starting value for the mean value $\overline{PG}$ of the plethysmographic signal. Mean value correction must take place reliably before each measurement run and is performed in the following way:

Mean value correction proper is carried out by the difference amplifier 11, which is pre-supplied with a certain mean value $\overline{PG}$ as an initial value. The difference amplifier 11 generates the PG-signal by subtracting the light signal from which ambient light has already been removed, from the pre-supplied mean value $\overline{PG}$. The difference amplifier 11 not only carries out mean value correction, but also amplifies and inverts the PG-signal, which is then fed into a comparator circuit. The comparator circuit consists of an upper comparator 42, a lower comparator 43 and a voltage divider with resistors 44, 45, 46, which defines threshold values. If the PG-signal generated by the difference amplifier 11 exceeds the threshold value of the upper comparator 42, this indicates that the pre-supplied mean value $\overline{PG}$ has been chosen too high. This is communicated to the unit PG Control 47, which decreases the mean value $\overline{PG}$ until the PG-signal is below the threshold value of the upper comparator 42. If, on the other hand, the PG-signal generated by the difference amplifier 11 is smaller than the threshold value of the lower comparator 43, the pre-supplied mean value is too low. In this case the unit PG Control 47 will increase the mean value $\overline{PG}$ until the PG-signal lies above the threshold of the lower comparator 43.

The control system shown in FIG. 4 also contains a Peak Detector 48 for determining the maximum amplitude of the PG-signal, which occurs, as is well known, when the pressure BP in the cuff 6 is approximately equal to the mean blood pressure. Thus the Peak Detector 48 may be used to find the mean blood pressure. To this end the pressure BP in the cuff 6 is varied until the maximum amplitude of the PG-signal occurs. The maximum amplitude of the PG-signal obtained is now assessed, since it also depends on the properties of the extremity E of each patient. If the amplitude is too small, the unit LED Control 33 is instructed to increase the current and thereby the light intensity of the LED 8. Conversely, if the maximum amplitude of the PG-signal is too large, the LED Control unit 33 is instructed to reduce the current through the LED 8.

When the cuff pressure BP at which the amplitude of the PG-signal is at its maximum, has been found, the optimum current for LED 8 can be determined—as described above— and the interfering mean value $\overline{PG}$ may be eliminated from the PG-signal in an optimal way by means of the comparator circuit 42-47 described above. The obtained pressure BP also corresponds to the optimum initial value of the set-point SP, because a variation of the pressure BP is mainly effected by a change in SP, with the control amplifications P, I and D set to zero.

Finally the invention proposes a means for computing an initial value for the set-point signal or the set-point SP.

To determine an optimum set-point value SP the following procedure is preferably used: After
1. the pressure BP in the cuff 6 has been changed by a variation of SP in such a way that the Peak Detector 48 has found the maximum amplitude of the PG-signal, and
2. the optimum current for LED 8 has been found, and
3. the interfering mean value $\overline{PG}$ has been optimally eliminated from the PG-signal, the amplification control unit 17 (FIG. 2) computes P, I and D from the maximum amplitude of the PG-signal and closes control loop 2. Pressure in the cuff 6 starts to pulsate and in accordance with the imposed control condition the PG-signal is held constant. Now SP is again varied. The systole/diastole detector 15 demarcates each heart cycle and associates it with the corresponding SP, so that it may be assessed for determination of the optimum SP. Preferably a typical heart cycle for each different SP is used for assessment. The following criteria may be used for assessment: the amplitude of BP, the ratio of mean pressure to pressure amplitude, the ratio of mean pressure to diastolic pressure, pressure rise or decay, temporal relationships etc. In accordance with the fuzzy logic in control loop 19 the following fuzzy criteria can be formulated and the heart beats or heart cycles may be assessed accordingly:

the BP amplitude of the heart cycle considered is in the range of maximum BP amplitudes the ratio of mean pressure to pressure amplitude lies in the physiological range the ratio of mean pressure to diastolic pressure lies in the physiological range pressure rise and pressure decay are in the physiological range temporal relationships are in the physiological range and so on.

In accordance with these fuzzy criteria each heart cycle may be assessed, for instance by using a simple scoring system. The heart cycle with the best score has the optimum SP, ties are resolved by using the mean value of the optimum SPs. In this way the optimum starting value of the set-point, or the set-point signal SP, can be found and communicated to all concentric control loops. The measurement proper may now begin, since all initial values of the control loop, SP, $\overline{PG}$, P, I, D and the optimum LED current, have been determined. These values are now monitored and, if necessary, readjusted by all concentric controllers and long-time continuous measurement of blood pressure is made possible.

The invention claimed is:

1. A method for controlling the pressure in at least one inflatable cuff of a blood pressure measuring apparatus in closed-loop operation, where the pressure on the cuff equals the arterial pressure, with a plethysmographic sensor device, whereby a plethysmographic signal PG and a cuff pressure signal BP are obtained, comprising the following steps:
   a) in a first concentric inner control loop the cuff pressure signal BP is used as control variable and is fed into a difference amplifier as a first input signal,
   b) in a second concentric outer control loop, which is simultaneously active with the first concentric inner control loop for closed-loop operation, the plethysmographic signal PG, with its mean value $\overline{PG}$ suppressed, is fed into a controller and is added to a set-point signal SP, and a target signal SW is generated, which is fed into said difference amplifier as a second input signal, c) an output signal AS of the difference amplifier is used to control at least one valve connected to a pressure source, which in turn regulates the pressure in the cuff, and d) no re-adjustments of set-point signal SP during open-loop operation with the help of a state-switch and timing-circuits.

2. The method according to claim 1, wherein the mean value $\overline{PG}$ of the plethysmographic signal PG is determined in a third concentric control loop, which is simultaneously active with the first concentric inner control loop during closed-loop operation, and continuously corrected as input signal of the second control loop.

3. The method according to claim 1, wherein the amplification parameters P, I and/or D are optimized in a fourth concentric control loop, which is simultaneously active with the first concentric inner control loop during closed-loop operation, and by means of the plethysmographic signal PG and the cuff pressure signal BP, and are continuously corrected as inputs to the controller.

4. The method according to claim 1, wherein in a fifth concentric control loop, which is simultaneously active with the first concentric inner control loop during closed-loop operation, the set-point signal SP is readjusted, depending on the integral of the plethysmographic signal PG.

5. The method according to claim 1, wherein in a sixth concentric control loop, which is simultaneously active with the first concentric inner control loop during closed-loop operation, the set-point signal SP is readjusted on the basis of derived quantities, such as amplitude, mean value or wave form of the plethysmographic signal PG and the cuff pressure signal BP, using a fuzzy-logic-approach.

6. The method according to claim 1, wherein in a seventh concentric control loop, which is simultaneously active with the first concentric inner control loop during closed-loop operation, the set-point signal SP is readjusted in dependence of the pulse waveform of the cuff pressure signal BP.

7. The method according to claim 1, wherein in an eighth concentric control loop, which is simultaneously active with the first concentric inner control loop during closed-loop operation, the set-point signal SP is readjusted by means of neural networks, auto-regressive models or self-learning models.

8. A device for controlling the pressure in at least one inflatable cuff of a blood pressure measuring apparatus in closed-loop operation, where the pressure in the cuff equals the arterial pressure, comprising a plethysmographic sensor device for obtaining a plethysmographic signal PG and a pressure sensor for obtaining a cuff pressure signal BP, including two concentric control loops, which are simultaneously active during closed-loop operation, acting on a difference amplifier, the first concentric inner control loop uses the cuff pressure signal BP as a first control variable and the second concentric outer control loop includes a controller which generates a target variable SW from the plethysmographic signal PG as a second control variable, and wherein the output of the difference amplifier controls at least one valve connected to a pressure source, thereby regulating the pressure in the cuff.

9. The device according to claim 8, wherein the second concentric control loop, which is simultaneously active during closed-loop operation, is provided with a difference amplifier which subtracts the plethysmographic signal PG from its mean value $\overline{PG}$, and with a summation unit adding a set-point signal SP.

10. The device according to claim 9, wherein a device is provided for computing an initial value for the mean value of the plethysmographic signal.

11. The device according to claim 9, wherein a device is provided for computing an initial value for the set-point signal SP.

12. The device according to claim 8, wherein said difference amplifier controls an inlet valve connected to a pressure source via a non-inverting amplifier unit and an outlet valve via an inverting amplifier unit, said valves being pressure-connected to the inflatable cuff.

13. The device according to claim 8, wherein said valves being pressure-connected to the inflatable cuff are designed as proportional valves.

14. The device according to claim 8, wherein said difference amplifier is designed as a comparator which actuates at least one digital switching valve for pressure regulation in the cuff.

15. The device according to claim 8, wherein the plethysmographic sensor is furnished with a device for the elimination of stray light or ambient light from the plethysmographic signal PG.

16. The device according to claim 8, wherein the light source of the plethysmographic sensor is furnished with circuitry for controlling its voltage or current.

17. The device according to claim 8, wherein said at least one inflatable cuff is a finger cuff.

18. The device according to claim 8, wherein said controller is a proportional-integral-differential PID-controller.

* * * * *